(12) United States Patent
Perron

(10) Patent No.: US 9,050,165 B2
(45) Date of Patent: Jun. 9, 2015

(54) REMOTELY ADJUSTABLE GASTRIC BANDING SYSTEM

(71) Applicant: Apollo Endosurgery, Inc., Austin, TX (US)

(72) Inventor: Christian Y. Perron, Ventura, CA (US)

(73) Assignee: APOLLO ENDOSURGERY, INC., Austin, TX (US)

( * ) Notice: Subject to any disclaimer, the term of this patent is extended or adjusted under 35 U.S.C. 154(b) by 0 days.

(21) Appl. No.: 13/905,019

(22) Filed: May 29, 2013

(65) Prior Publication Data

US 2013/0261384 A1    Oct. 3, 2013

Related U.S. Application Data

(63) Continuation of application No. 12/877,046, filed on Sep. 7, 2010, now abandoned.

(51) Int. Cl.
   *A61F 5/00* (2006.01)
(52) U.S. Cl.
   CPC .............. *A61F 5/0059* (2013.01); *A61F 5/0056* (2013.01)
(58) Field of Classification Search
   CPC .......... A61F 5/005; A61F 2/04; A61F 5/0053
   USPC ......... 600/29–31, 37; 128/897–899, 901, 904
   See application file for complete search history.

(56) References Cited

U.S. PATENT DOCUMENTS

| | | |
|---|---|---|
| 1,174,814 A | 3/1916 | Brennan |
| 1,830,947 A | 11/1931 | Klingel |
| 1,999,683 A | 4/1935 | Borresen |

(Continued)

FOREIGN PATENT DOCUMENTS

| | | |
|---|---|---|
| CA | 949965 | 6/1974 |
| CN | 1250382 A | 4/2000 |

(Continued)

OTHER PUBLICATIONS

Acuna-Goycolea et al.; 'Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus'; The Journal of Neuroscience; V. 25(32); pp. 7406-7419; Aug. 10, 2005.

(Continued)

*Primary Examiner* — Christine H Matthews
*Assistant Examiner* — Joshua D Lannu
(74) *Attorney, Agent, or Firm* — Gordon & Jacobson, PC

(57) ABSTRACT

A fluid reservoir for use in a remotely adjustable gastric banding system comprises a housing and a flexible reservoir pouch positioned within the housing. The flexible reservoir pouch is coupled to an inflatable portion of a gastric band via flexible tubing. A pump coupled to the flexible reservoir pouch facilitates filling and draining the inflatable portion of the gastric band. The pump may be located within or outside of the housing. A receiving coil may be coupled to the housing, and the receiving coil forms a loop around the housing. The receiving coil receives radio frequency signals to drive the pump. A circuit board may be disposed in the housing for driving the pump to move the fluid between the flexible reservoir pouch and the inflatable portion of the gastric band. A portion of the circuit board may be a flexible circuit board to allow the housing to flex.

18 Claims, 4 Drawing Sheets

(56) References Cited

U.S. PATENT DOCUMENTS

| | | |
|---|---|---|
| 2,163,048 A | 6/1939 | McKee |
| 2,339,138 A | 1/1944 | Black |
| 2,405,667 A | 8/1946 | Andrew |
| 2,438,231 A | 3/1948 | Schultz |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck |
| 3,189,961 A | 6/1965 | Heller |
| 3,667,081 A | 6/1972 | Burger |
| 3,840,018 A | 10/1974 | Heifetz |
| 3,955,834 A | 5/1976 | Ahlrot |
| 4,053,176 A | 10/1977 | Hilbush |
| 4,118,805 A | 10/1978 | Reimels |
| 4,133,315 A | 1/1979 | Berman |
| 4,157,713 A | 6/1979 | Clarey |
| 4,176,412 A | 12/1979 | Peterson |
| 4,236,521 A | 12/1980 | Lauterjung |
| 4,271,827 A | 6/1981 | Angelchik |
| 4,299,012 A | 11/1981 | Oetiker |
| 4,340,083 A | 7/1982 | Cummins |
| 4,399,809 A | 8/1983 | Baro et al. |
| 4,408,597 A | 10/1983 | Tenney |
| 4,417,567 A | 11/1983 | Trick |
| 4,424,208 A | 1/1984 | Wallace |
| 4,442,153 A | 4/1984 | Meltsch |
| 4,450,375 A | 5/1984 | Siegal |
| 4,485,805 A | 12/1984 | Foster |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen |
| 4,582,640 A | 4/1986 | Smestad |
| 4,582,865 A | 4/1986 | Balazs |
| 4,592,339 A | 6/1986 | Kuzmak |
| 4,592,355 A | 6/1986 | Antebi |
| 4,601,713 A | 7/1986 | Fuqua |
| 4,667,672 A | 5/1987 | Romanowski |
| 4,671,351 A | 6/1987 | Rappe |
| 4,693,695 A | 9/1987 | Cheng |
| 4,694,827 A | 9/1987 | Weiner |
| 4,696,288 A | 9/1987 | Kuzmak |
| 4,708,140 A | 11/1987 | Baron |
| 4,716,154 A | 12/1987 | Maelson |
| 4,753,086 A | 6/1988 | Schmidt |
| 4,760,837 A | 8/1988 | Petit |
| 4,803,075 A | 2/1989 | Wallace |
| 4,881,939 A | 11/1989 | Newman |
| 4,883,467 A | 11/1989 | Franetzki |
| 4,886,787 A | 12/1989 | de Belder et al. |
| 4,896,787 A | 1/1990 | Delamour |
| 4,915,690 A | 4/1990 | Cone |
| 4,925,446 A | 5/1990 | Garay |
| 4,944,487 A | 7/1990 | Holtermann |
| 4,944,659 A | 7/1990 | Labbe |
| 4,958,791 A | 9/1990 | Nakamura |
| 4,969,899 A | 11/1990 | Cox |
| 4,994,019 A | 2/1991 | Fernandez |
| 5,045,060 A | 9/1991 | Melsky |
| 5,074,868 A | 12/1991 | Kuzmak |
| 5,084,061 A | 1/1992 | Gau |
| 5,091,171 A | 2/1992 | Yu |
| 5,116,652 A | 5/1992 | Alzner |
| 5,120,313 A | 6/1992 | Elftman |
| 5,143,724 A | 9/1992 | Leshchiner |
| 5,152,770 A | 10/1992 | Bengmark |
| 5,160,338 A | 11/1992 | Vincent |
| 5,188,609 A | 2/1993 | Bayless |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner |
| 5,259,399 A | 11/1993 | Brown |
| 5,326,349 A | 7/1994 | Baraff |
| 5,343,894 A | 9/1994 | Frisch |
| 5,356,883 A | 10/1994 | Kuo |
| 5,360,445 A | 11/1994 | Goldowsky |
| 5,391,156 A | 2/1995 | Hildwein |
| 5,399,351 A | 3/1995 | Leshchiner |
| 5,449,363 A | 9/1995 | Brust |
| 5,449,368 A | 9/1995 | Kuzmak |
| 5,458,568 A | 10/1995 | Racchini |
| 5,509,888 A | 4/1996 | Miller |
| 5,531,716 A | 7/1996 | Luzio |
| 5,535,752 A | 7/1996 | Halperin |
| 5,554,113 A | 9/1996 | Novak |
| 5,562,714 A | 10/1996 | Grevious |
| 5,601,604 A | 2/1997 | Vincent |
| 5,607,418 A | 3/1997 | Arzbaecher |
| 5,633,001 A | 5/1997 | Ågerup |
| 5,653,718 A | 8/1997 | Yoon |
| 5,658,298 A | 8/1997 | Vincent |
| 5,676,162 A | 10/1997 | Larson |
| 5,695,504 A | 12/1997 | Gifford |
| 5,704,893 A | 1/1998 | Timm |
| 5,713,911 A | 2/1998 | Racenet |
| 5,733,257 A | 3/1998 | Sternby |
| 5,748,200 A | 5/1998 | Funahashi |
| 5,766,232 A | 6/1998 | Grevious |
| 5,769,877 A | 6/1998 | Barreras |
| 5,785,295 A | 7/1998 | Tsai |
| 5,817,113 A | 10/1998 | Gifford |
| 5,827,529 A | 10/1998 | Ono |
| 5,833,698 A | 11/1998 | Hinchliffe |
| 5,861,014 A | 1/1999 | Familoni |
| RE36,176 E | 3/1999 | Kuzmak |
| 5,886,042 A | 3/1999 | Yu |
| 5,904,697 A | 5/1999 | Gifford |
| 5,910,149 A | 6/1999 | Kuzmak |
| 5,928,195 A | 7/1999 | Malamud |
| 5,938,669 A | 8/1999 | Klaiber |
| 5,944,696 A | 8/1999 | Bayless |
| 5,944,751 A | 8/1999 | Laub |
| 5,993,473 A | 11/1999 | Chan |
| 6,009,350 A * | 12/1999 | Renken ............ 607/32 |
| 6,013,679 A | 1/2000 | Kuo |
| 6,024,340 A | 2/2000 | Lazarus |
| 6,024,704 A | 2/2000 | Meador |
| 6,048,309 A | 4/2000 | Flom |
| 6,067,991 A * | 5/2000 | Forsell ............ 128/899 |
| 6,074,341 A | 6/2000 | Anderson |
| 6,074,378 A | 6/2000 | Mouri |
| 6,083,249 A | 7/2000 | Familoni |
| 6,090,131 A | 7/2000 | Daley |
| 6,102,678 A | 8/2000 | Peclat |
| 6,102,922 A | 8/2000 | Jakobsson |
| 6,171,321 B1 | 1/2001 | Gifford |
| 6,193,734 B1 | 2/2001 | Bolduc |
| 6,203,523 B1 | 3/2001 | Haller et al. |
| 6,210,345 B1 | 4/2001 | Van Brunt |
| 6,210,347 B1 | 4/2001 | Forsell |
| 6,221,024 B1 | 4/2001 | Miesel |
| 6,224,857 B1 | 5/2001 | Romeo |
| 6,306,088 B1 | 10/2001 | Krausman |
| 6,327,503 B1 | 12/2001 | Familoni |
| 6,371,965 B2 | 4/2002 | Gifford |
| 6,372,494 B1 | 4/2002 | Naughton |
| 6,383,218 B1 | 5/2002 | Sourdile |
| 6,383,219 B1 | 5/2002 | Telandro |
| 6,387,105 B1 | 5/2002 | Gifford |
| 6,417,750 B1 | 7/2002 | Sohn |
| 6,418,934 B1 | 7/2002 | Chin |
| 6,419,696 B1 | 7/2002 | Ortiz |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford |
| 6,450,173 B1 | 9/2002 | Forsell |
| 6,450,946 B1 | 9/2002 | Forsell |
| 6,451,034 B1 | 9/2002 | Gifford |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |

(56) References Cited

U.S. PATENT DOCUMENTS

| | | |
|---|---|---|
| 6,454,785 B2 | 9/2002 | De Hoyos |
| 6,457,801 B1 | 10/2002 | Fish |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B2 | 11/2002 | Ekich |
| 6,475,136 B1 | 11/2002 | Forsell |
| 6,485,496 B1 | 11/2002 | Suyker |
| 6,491,704 B2 | 12/2002 | Gifford |
| 6,491,705 B2 | 12/2002 | Gifford |
| 6,511,490 B2 | 1/2003 | Robert |
| 6,517,556 B1 | 2/2003 | Monassevitch |
| 6,527,701 B1 | 3/2003 | Sayet |
| 6,547,801 B1 | 4/2003 | Dargent |
| 6,565,582 B2 | 5/2003 | Gifford |
| 6,579,301 B1 | 6/2003 | Bales |
| 6,601,604 B1 | 8/2003 | Cooper |
| 6,615,084 B1 | 9/2003 | Cigaina |
| 6,627,620 B1 | 9/2003 | Nielsen |
| 6,630,486 B1 | 10/2003 | Royer |
| 6,632,239 B2 | 10/2003 | Snyder |
| 6,646,628 B2 | 11/2003 | Shirochi |
| 6,676,674 B1 | 1/2004 | Dudai |
| 6,685,668 B1 | 2/2004 | Cho |
| 6,685,963 B1 | 2/2004 | Taupin |
| 6,691,047 B1 | 2/2004 | Fredericks |
| 6,715,731 B1 | 4/2004 | Post |
| 6,729,600 B2 | 5/2004 | Mattes |
| 6,754,527 B2 | 6/2004 | Stroebel |
| 6,767,924 B2 | 7/2004 | Yu |
| 6,791,447 B2 * | 9/2004 | Scheible et al. ............ 336/221 |
| 6,811,136 B2 | 11/2004 | Eberhardt |
| 6,820,651 B2 | 11/2004 | Seuret |
| 6,834,201 B2 | 12/2004 | Gillies |
| 6,871,090 B1 | 3/2005 | He |
| 6,889,086 B2 | 5/2005 | Mass |
| 6,916,326 B2 | 7/2005 | Benchetrit |
| 6,921,819 B2 | 7/2005 | Piron |
| 6,924,273 B2 | 8/2005 | Pierce |
| 6,940,467 B2 | 9/2005 | Fischer |
| 6,966,875 B1 | 11/2005 | Longobardi |
| 6,997,914 B2 * | 2/2006 | Smith et al. ............ 604/288.04 |
| 7,017,583 B2 | 3/2006 | Forsell |
| 7,021,147 B1 | 4/2006 | Subramanian |
| 7,037,344 B2 | 5/2006 | Kagan |
| 7,040,349 B2 | 5/2006 | Moler |
| 7,054,690 B2 | 5/2006 | Imran |
| 7,058,434 B2 | 6/2006 | Wang |
| 7,060,080 B2 | 6/2006 | Bachmann |
| 7,066,486 B2 | 6/2006 | Lee |
| 7,118,526 B2 | 10/2006 | Egle |
| 7,119,062 B1 | 10/2006 | Alvis |
| 7,128,750 B1 | 10/2006 | Stergiopulos |
| 7,144,400 B2 | 12/2006 | Byrum |
| 7,172,607 B2 | 2/2007 | Hofle |
| 7,177,693 B2 | 2/2007 | Starkebaum |
| 7,191,007 B2 * | 3/2007 | Desai et al. ............... 607/33 |
| 7,204,821 B1 | 4/2007 | Clare |
| 7,223,239 B2 | 5/2007 | Schulze |
| 7,238,191 B2 | 7/2007 | Bachmann |
| 7,240,607 B2 | 7/2007 | Fish |
| 7,255,675 B2 | 8/2007 | Gertner |
| 7,263,405 B2 | 8/2007 | Boveja |
| 7,282,023 B2 | 10/2007 | Frering |
| 7,288,064 B2 | 10/2007 | Boustani |
| 7,297,103 B2 | 11/2007 | Jarsaillon |
| 7,299,082 B2 | 11/2007 | Feldman |
| 7,310,557 B2 | 12/2007 | Maschino |
| 7,311,716 B2 | 12/2007 | Byrum |
| 7,311,717 B2 | 12/2007 | Egle |
| 7,314,443 B2 | 1/2008 | Jordan |
| 7,314,636 B2 | 1/2008 | Caseres |
| 7,338,433 B2 | 3/2008 | Coe |
| 7,340,306 B2 | 3/2008 | Barrett |
| 7,351,198 B2 | 4/2008 | Byrum |
| 7,351,240 B2 | 4/2008 | Hassler |
| 7,364,542 B2 | 4/2008 | Jambor |
| 7,367,340 B2 | 5/2008 | Nelson |
| 7,367,937 B2 | 5/2008 | Jambor |
| 7,374,565 B2 | 5/2008 | Hassler |
| 7,390,294 B2 | 6/2008 | Hassler |
| 7,396,353 B2 | 7/2008 | Lorenzen |
| 7,416,528 B2 | 8/2008 | Crawford |
| 7,457,668 B2 | 11/2008 | Cancel |
| 7,481,763 B2 | 1/2009 | Hassler |
| 7,500,944 B2 | 3/2009 | Byrum |
| 7,502,649 B2 | 3/2009 | Ben-Haim |
| 7,530,943 B2 | 5/2009 | Lechner |
| 7,594,885 B2 | 9/2009 | Byrum |
| 7,599,743 B2 | 10/2009 | Hassler |
| 7,599,744 B2 | 10/2009 | Giordano |
| 7,601,162 B2 | 10/2009 | Hassler |
| 7,615,001 B2 | 11/2009 | Jambor |
| 7,618,365 B2 | 11/2009 | Jambor |
| 7,658,196 B2 | 2/2010 | Ferreri |
| 7,670,279 B2 | 3/2010 | Gertner |
| 7,699,770 B2 | 4/2010 | Hassler |
| 7,712,470 B2 | 5/2010 | Gertner |
| 7,727,141 B2 | 6/2010 | Hassler |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler |
| 7,775,966 B2 | 8/2010 | Dlugos |
| 7,775,967 B2 | 8/2010 | Gertner |
| 7,794,386 B2 | 9/2010 | Brooks |
| 7,811,298 B2 | 10/2010 | Birk |
| 7,824,422 B2 | 11/2010 | Benchetrit |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos |
| 7,862,502 B2 | 1/2011 | Pool |
| 7,879,068 B2 | 2/2011 | Dlugos |
| 7,951,067 B2 | 5/2011 | Byrum |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0193679 A1 | 12/2002 | Malave |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0060873 A1 | 3/2003 | Gertner |
| 2003/0066536 A1 | 4/2003 | Forsell |
| 2003/0073880 A1 | 4/2003 | Polsky |
| 2003/0093157 A1 | 5/2003 | Casares |
| 2003/0100910 A1 | 5/2003 | Gifford |
| 2003/0120288 A1 | 6/2003 | Benchetrit |
| 2003/0148995 A1 | 8/2003 | Piron |
| 2003/0158564 A1 | 8/2003 | Benchetrit |
| 2003/0158569 A1 | 8/2003 | Wazne |
| 2003/0181890 A1 | 9/2003 | Schulze |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 | 3/2004 | Benchetrit |
| 2004/0059393 A1 | 3/2004 | Policker |
| 2004/0068847 A1 | 4/2004 | Belisle |
| 2004/0106899 A1 | 6/2004 | McMichael |
| 2004/0133219 A1 | 7/2004 | Forsell |
| 2004/0147816 A1 | 7/2004 | Policker |
| 2004/0148034 A1 | 7/2004 | Kagan |

(56) References Cited

U.S. PATENT DOCUMENTS

| | | |
|---|---|---|
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon |
| 2004/0254537 A1 | 12/2004 | Conlon |
| 2004/0260319 A1 | 12/2004 | Egle |
| 2004/0267288 A1 | 12/2004 | Byrum |
| 2004/0267291 A1 | 12/2004 | Byrum |
| 2004/0267292 A1 | 12/2004 | Byrum |
| 2004/0267293 A1 | 12/2004 | Byrum |
| 2004/0267377 A1 | 12/2004 | Egle |
| 2005/0002984 A1 | 1/2005 | Byrum |
| 2005/0038484 A1 | 2/2005 | Knudson |
| 2005/0038498 A1 | 2/2005 | Dubrow |
| 2005/0055039 A1 | 3/2005 | Burnett |
| 2005/0070934 A1 | 3/2005 | Tanaka |
| 2005/0070937 A1 | 3/2005 | Jambor |
| 2005/0082793 A1 | 4/2005 | Lee |
| 2005/0100779 A1 | 5/2005 | Gertner |
| 2005/0104457 A1 | 5/2005 | Jordan |
| 2005/0119672 A1 | 6/2005 | Benchetrit |
| 2005/0119674 A1 | 6/2005 | Gingras |
| 2005/0131383 A1 | 6/2005 | Chen |
| 2005/0131485 A1 | 6/2005 | Knudson |
| 2005/0136122 A1 | 6/2005 | Sadozai |
| 2005/0142152 A1 | 6/2005 | Leshchiner |
| 2005/0143765 A1 | 6/2005 | Bachmann |
| 2005/0143766 A1 | 6/2005 | Bachmann |
| 2005/0154274 A1 | 7/2005 | Jarsaillon |
| 2005/0171568 A1 | 8/2005 | Duffy |
| 2005/0183730 A1 | 8/2005 | Byrum |
| 2005/0192531 A1 | 9/2005 | Birk |
| 2005/0192601 A1 | 9/2005 | Demarais |
| 2005/0192629 A1 | 9/2005 | Saadat |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler |
| 2005/0267500 A1 | 12/2005 | Hassler |
| 2005/0267533 A1 | 12/2005 | Gertner |
| 2005/0271729 A1 | 12/2005 | Wang |
| 2005/0277899 A1 | 12/2005 | Conlon |
| 2005/0283041 A1 | 12/2005 | Egle |
| 2005/0288739 A1 | 12/2005 | Hassler |
| 2005/0288740 A1 | 12/2005 | Hassler |
| 2005/0288743 A1* | 12/2005 | Ahn et al. .................. 607/61 |
| 2006/0015138 A1 | 1/2006 | Gertner |
| 2006/0020298 A1 | 1/2006 | Camilleri |
| 2006/0041183 A1 | 2/2006 | Massen |
| 2006/0074439 A1 | 4/2006 | Garner |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman |
| 2006/0142790 A1 | 6/2006 | Gertner |
| 2006/0161139 A1 | 7/2006 | Levine |
| 2006/0161186 A1 | 7/2006 | Hassler |
| 2006/0167531 A1 | 7/2006 | Gertner |
| 2006/0173238 A1 | 8/2006 | Starkebaum |
| 2006/0173424 A1 | 8/2006 | Conlon |
| 2006/0183967 A1 | 8/2006 | Lechner |
| 2006/0189887 A1 | 8/2006 | Hassler |
| 2006/0189888 A1 | 8/2006 | Hassler |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler |
| 2006/0211912 A1 | 9/2006 | Dlugos |
| 2006/0211913 A1 | 9/2006 | Dlugos |
| 2006/0211914 A1 | 9/2006 | Hassler |
| 2006/0212051 A1 | 9/2006 | Snyder |
| 2006/0212053 A1 | 9/2006 | Gertner |
| 2006/0235448 A1 | 10/2006 | Roslin |
| 2006/0246137 A1 | 11/2006 | Hermitte |
| 2006/0247721 A1 | 11/2006 | Maschino |
| 2006/0247722 A1 | 11/2006 | Maschino |
| 2006/0252982 A1 | 11/2006 | Hassler |
| 2006/0252983 A1 | 11/2006 | Lembo |
| 2006/0257488 A1 | 11/2006 | Hubbard |
| 2006/0264699 A1 | 11/2006 | Gertner |
| 2006/0276812 A1 | 12/2006 | Hill |
| 2006/0293627 A1 | 12/2006 | Byrum |
| 2007/0015954 A1 | 1/2007 | Dlugos |
| 2007/0015955 A1 | 1/2007 | Tsonton |
| 2007/0015956 A1 | 1/2007 | Crawford |
| 2007/0016231 A1 | 1/2007 | Jambor |
| 2007/0016262 A1 | 1/2007 | Gross |
| 2007/0027356 A1 | 2/2007 | Ortiz |
| 2007/0027358 A1 | 2/2007 | Gertner |
| 2007/0044655 A1 | 3/2007 | Fish |
| 2007/0077292 A1 | 4/2007 | Pinsky |
| 2007/0078476 A1 | 4/2007 | Hull |
| 2007/0125826 A1 | 6/2007 | Shelton |
| 2007/0156013 A1* | 7/2007 | Birk ............................ 600/37 |
| 2007/0167672 A1 | 7/2007 | Dlugos |
| 2007/0167982 A1 | 7/2007 | Gertner |
| 2007/0173685 A1 | 7/2007 | Jambor |
| 2007/0173888 A1 | 7/2007 | Gertner |
| 2007/0179335 A1 | 8/2007 | Gertner |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann |
| 2007/0250086 A1 | 10/2007 | Wiley |
| 2007/0255335 A1 | 11/2007 | Herbert |
| 2007/0255336 A1 | 11/2007 | Herbert |
| 2007/0265598 A1 | 11/2007 | Karasik |
| 2007/0265645 A1 | 11/2007 | Birk |
| 2007/0265646 A1 | 11/2007 | McCoy |
| 2007/0293716 A1 | 12/2007 | Baker |
| 2007/0298005 A1 | 12/2007 | Thibault |
| 2008/0009680 A1 | 1/2008 | Hassler |
| 2008/0015406 A1 | 1/2008 | Dlugos |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang |
| 2008/0108862 A1 | 5/2008 | Jordan |
| 2008/0147002 A1 | 6/2008 | Gertner |
| 2008/0161717 A1 | 7/2008 | Gertner |
| 2008/0161875 A1 | 7/2008 | Stone |
| 2008/0167647 A1 | 7/2008 | Gertner |
| 2008/0167648 A1 | 7/2008 | Gertner |
| 2008/0172072 A1 | 7/2008 | Pool |
| 2008/0188766 A1 | 8/2008 | Gertner |
| 2008/0195092 A1 | 8/2008 | Kim |
| 2008/0208240 A1 | 8/2008 | Paz |
| 2008/0221598 A1 | 9/2008 | Dlugos |
| 2008/0243071 A1 | 10/2008 | Quijano |
| 2008/0249806 A1 | 10/2008 | Dlugos |
| 2008/0250340 A1 | 10/2008 | Dlugos |
| 2008/0250341 A1 | 10/2008 | Dlugos |
| 2008/0255403 A1 | 10/2008 | Voegele |
| 2008/0255414 A1 | 10/2008 | Voegele |
| 2008/0255425 A1 | 10/2008 | Voegele |
| 2008/0255459 A1 | 10/2008 | Voegele |
| 2008/0255537 A1 | 10/2008 | Voegele |

(56) References Cited

U.S. PATENT DOCUMENTS

| | | |
|---|---|---|
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton |
| 2008/0287974 A1 | 11/2008 | Widenhouse |
| 2008/0287976 A1 | 11/2008 | Weaner |
| 2008/0300618 A1 | 12/2008 | Gertner |
| 2008/0319435 A1 | 12/2008 | Rioux |
| 2009/0054914 A1 | 2/2009 | Lechner |
| 2009/0062825 A1 | 3/2009 | Pool |
| 2009/0062826 A1 | 3/2009 | Steffen |
| 2009/0082793 A2 | 3/2009 | Birk |
| 2009/0118572 A1 | 5/2009 | Lechner |
| 2009/0149874 A1 | 6/2009 | Ortiz |
| 2009/0157106 A1 | 6/2009 | Marcotte |
| 2009/0157107 A1 | 6/2009 | Kierath |
| 2009/0157113 A1 | 6/2009 | Marcotte |
| 2009/0171375 A1 | 7/2009 | Coe |
| 2009/0171378 A1 | 7/2009 | Coe |
| 2009/0171379 A1 | 7/2009 | Coe |
| 2009/0187202 A1 | 7/2009 | Ortiz |
| 2009/0192404 A1 | 7/2009 | Ortiz |
| 2009/0192415 A1 | 7/2009 | Ortiz |
| 2009/0192533 A1 | 7/2009 | Dlugos |
| 2009/0192534 A1 | 7/2009 | Ortiz |
| 2009/0192541 A1 | 7/2009 | Ortiz |
| 2009/0198261 A1 | 8/2009 | Schweikert |
| 2009/0202387 A1 | 8/2009 | Dlugos |
| 2009/0204131 A1 | 8/2009 | Ortiz |
| 2009/0204132 A1 | 8/2009 | Ortiz |
| 2009/0209995 A1 | 8/2009 | Byrum |
| 2009/0216255 A1 | 8/2009 | Coe |
| 2009/0220176 A1 | 9/2009 | Fusco |
| 2009/0222031 A1 | 9/2009 | Axelsson |
| 2009/0222065 A1 | 9/2009 | Dlugos |
| 2009/0228063 A1 | 9/2009 | Dlugos |
| 2009/0228072 A1 | 9/2009 | Coe |
| 2009/0270904 A1 | 10/2009 | Birk |
| 2009/0306462 A1 | 12/2009 | Lechner |
| 2010/0010291 A1 | 1/2010 | Birk |
| 2010/0049224 A1 | 2/2010 | Vargas |
| 2010/0087843 A1 | 4/2010 | Bertolote |
| 2010/0099945 A1 | 4/2010 | Birk |
| 2010/0100079 A1 | 4/2010 | Berkcan |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk |
| 2010/0191265 A1 | 7/2010 | Lau |
| 2010/0191271 A1 | 7/2010 | Lau |
| 2010/0204647 A1 | 8/2010 | Gertner |
| 2010/0204723 A1 | 8/2010 | Gertner |
| 2010/0217071 A1 | 8/2010 | Ricol |
| 2010/0226988 A1 | 9/2010 | Lebreton |
| 2010/0228080 A1 | 9/2010 | Tavori |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk |
| 2010/0312046 A1 | 12/2010 | Lau |
| 2010/0312147 A1 | 12/2010 | Gertner |
| 2010/0324358 A1 | 12/2010 | Birk |
| 2010/0324359 A1 | 12/2010 | Birk |
| 2011/0201874 A1 | 8/2011 | Birk |

FOREIGN PATENT DOCUMENTS

| | | |
|---|---|---|
| CN | 1367670 A | 9/2002 |
| DE | 4225524 | 2/1994 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 A2 | 9/2000 |
| EP | 1072282 | 1/2001 |
| EP | 1105073 | 6/2001 |
| EP | 1396242 A1 | 3/2004 |
| EP | 1396243 A1 | 3/2004 |
| EP | 1491167 | 12/2004 |
| EP | 1491168 | 12/2004 |
| EP | 1529502 | 5/2005 |
| EP | 1547549 A2 | 6/2005 |
| EP | 1574189 | 9/2005 |
| EP | 1600183 A1 | 11/2005 |
| EP | 1602346 A1 | 12/2005 |
| EP | 1704833 A2 | 9/2006 |
| EP | 1719480 A2 | 11/2006 |
| EP | 1736123 A1 | 12/2006 |
| EP | 1736195 | 12/2006 |
| EP | 1736202 | 12/2006 |
| EP | 1743605 A1 | 1/2007 |
| EP | 1829504 | 9/2007 |
| EP | 1829505 | 9/2007 |
| EP | 1829506 | 9/2007 |
| EP | 1967168 A2 | 9/2008 |
| EP | 1992315 | 11/2008 |
| EP | 2074970 A1 | 7/2009 |
| EP | 2074971 A1 | 7/2009 |
| EP | 2074972 A2 | 7/2009 |
| EP | 2095796 A1 | 9/2009 |
| EP | 2095798 | 9/2009 |
| EP | 2191796 | 6/2010 |
| FR | 1566202 | 5/1969 |
| FR | 2688693 | 9/1993 |
| FR | 2769491 | 4/1999 |
| FR | 2783153 | 3/2000 |
| FR | 2797181 A1 | 2/2001 |
| FR | 2799118 | 4/2001 |
| FR | 2823663 A1 | 10/2002 |
| FR | 2855744 A1 | 12/2004 |
| FR | 2921822 A1 | 4/2009 |
| GB | 1174814 A | 12/1969 |
| GB | 2090747 | 7/1982 |
| JP | 57171676 | 10/1982 |
| JP | 167309 | 4/1989 |
| JP | 2019147 | 1/1990 |
| JP | 2132104 | 11/1990 |
| JP | 3105702 | 11/1991 |
| JP | 11244395 | 9/1999 |
| JP | 2003526410 | 9/2003 |
| JP | 2005131380 | 5/2005 |
| JP | 2005334658 | 12/2005 |
| SE | 8503144 | 12/1986 |
| WO | 8600079 | 1/1986 |
| WO | 8600912 | 2/1986 |
| WO | 8911701 | 11/1989 |
| WO | 9000369 | 1/1990 |
| WO | 9220349 | 11/1992 |
| WO | 9402517 | 2/1994 |
| WO | 9633751 | 1/1996 |
| WO | 9835639 | 8/1998 |
| WO | 9835640 | 8/1998 |
| WO | 0000108 A1 | 1/2000 |
| WO | 0001428 | 1/2000 |
| WO | 0009047 A1 | 2/2000 |
| WO | 0009049 | 2/2000 |
| WO | 0015158 A1 | 3/2000 |
| WO | 0066196 | 11/2000 |
| WO | 0110359 A1 | 2/2001 |
| WO | 0112078 A1 | 2/2001 |
| WO | 0141671 | 6/2001 |
| WO | 0147435 | 7/2001 |
| WO | 0147575 A2 | 7/2001 |
| WO | 0149245 A2 | 7/2001 |
| WO | 0152777 | 7/2001 |
| WO | 0168007 | 9/2001 |
| WO | 0185071 | 11/2001 |
| WO | 0205753 | 1/2002 |
| WO | 0209792 | 2/2002 |

(56) References Cited

FOREIGN PATENT DOCUMENTS

| | | |
|---|---|---|
| WO | 0219953 | 3/2002 |
| WO | 0226317 | 4/2002 |
| WO | 02053093 | 7/2002 |
| WO | 02065948 | 8/2002 |
| WO | 02096326 | 12/2002 |
| WO | 03007782 | 1/2003 |
| WO | 03055420 | 7/2003 |
| WO | 03057092 | 7/2003 |
| WO | 03059215 | 7/2003 |
| WO | 03077191 | 9/2003 |
| WO | 03101352 A1 | 12/2003 |
| WO | 03105732 A1 | 12/2003 |
| WO | 2004014245 A1 | 2/2004 |
| WO | 2004019671 A2 | 3/2004 |
| WO | 2004108025 | 12/2004 |
| WO | 2004112563 A2 | 12/2004 |
| WO | 2005007232 | 1/2005 |
| WO | 2005009305 A1 | 2/2005 |
| WO | 2005067994 | 7/2005 |
| WO | 2005072195 | 8/2005 |
| WO | 2005087147 | 9/2005 |
| WO | 2005094447 | 10/2005 |
| WO | 2005112888 | 12/2005 |
| WO | 2006040647 | 4/2006 |
| WO | 2006049725 | 5/2006 |
| WO | 2006083885 | 8/2006 |
| WO | 2006108203 A2 | 10/2006 |
| WO | 2007067206 | 6/2007 |
| WO | 2007081304 A2 | 7/2007 |
| WO | 2007106727 A2 | 9/2007 |
| WO | 2007114905 | 10/2007 |
| WO | 2007145638 | 12/2007 |
| WO | 2008063673 A1 | 5/2008 |
| WO | 2008134755 | 11/2008 |
| WO | 2009050709 A2 | 4/2009 |
| WO | 2009132127 A1 | 10/2009 |
| WO | 2009136126 A2 | 11/2009 |
| WO | 2010042493 A1 | 4/2010 |

OTHER PUBLICATIONS

Adrian et al.; 'Mechanism of Pancreatic Polypeptide Release in Man.' The Lancet; pp. 161-163; Jan. 22, 1977.

Anson; 'Shape Memory Alloys—Medical Applications,' Source: Materials World, vol. 7, No. 12, pp. 745-747, Dec. 1999.

Asakawa et al; 'Antagonism of Ghrelin Receptor Reduces Food Intake and Body Weight Gain in Mice'; Gut.; V.52; pp. 947-952; 2003.

Baggio et al. 'Biology of Integrins: GLP-1 and GIP'; Gastroenrology; V. 132; pp. 2131-2157; 2007.

Ballantyne; 'Peptide YY(1-36) and Peptide YY(3-36): Part I. Distribution, Release, and Actions'; Obesity Surgery; V.16; pp. 651-658; 2006.

Ballantyne; "Peptide YY(1-36) and Peptide YY(3-36): Part II. Changes after Gastrointestinal Surgery and Bariatric Surgery"; Obesity Surgery; V.16; pp. 795-803; 2006.

Berne et al; 'Physiology'; V. 5; pp. 55-57, 210, 428, 540, 554, 579, 584, 591; 2004.

BioEnterics Corporation, an Inamed Company, BioEnterics Intragastric Balloon; Directions for Use Published Document, P/N 94200 Rev: B, pp. 1-56.

Bio Enterics Lap-Band Adjustable Gastric Banding System, Inamed Health, pub. Aug. 28, 2003, pp. 1-115.

Boulant et al.; 'Cholecystokinin in Transient Lower Oesophageal Sphincter Relation Due to Gastric Distension in Humans'; Gut; V. 40; pp. 575-581; 1997.

Bradjewin et al; 'Dose Ranging Study of the Effects of Cholecystokinin in Healthy Volunteers'; J. Psychiatr. Neurosci.; V. 16 (2); pp. 91-95; 1991.

Burdyga et al.; 'Cholecystokinin Regulates Expression of Y2 Receptors in Vagal Afferent Neurons Serving the Stomach'; The Journal of Neuroscience; V. 28; No. 45; pp. 11583-11592; Nov. 5, 2008.

Chaptini et al.; "Neuroendocrine Regulation of Food Intake"; Current Opinion in Gastroenterology; V. 24; pp. 223-229; 2008.

Chaudhri; 'Can Gut Hormones Control Appetite and Prevent Obesity?' Diabetes Care; V. 31; Supp 2; pp. S284-S289; Feb. 2008.

Cohen et al.; 'Oxyntomodulin Suppresses Appetite and Reduces Food in Humans'; J. Clin. Endocrinol. Metab.; V. 88; pp. 4696-4701; 2003.

Corno et al.; 'A new implantable device for telemetric control of pulmonary blood flow'; New ideas; received Apr. 24, 2004; received in revised form Jul. 12, 2002; 10 pages.

Corno et al.; 'FlowWatchTM in clipped and inclipped position'; Interact Cardio Vase Thorac Surg 2002; 1:46-49; Copyright@2002 The European Asociation for Cardio-thoracic Surgery; 1 page.

Cummings et al.; 'Plasma Ghrelin Levels After Diet-Induced Weight Loss or Gastric Bypass Surgery'; N. Engl J. Med; V. 346, No. 21; pp. 1623-1630; May 23, 2002.

Cummings; 'Gastrointestinal Regulation of Foot Intake'; The Food Journal of Clinical Investigation; V. 117, N. 1; pp. 13-23; Jan. 2007.

Dakin et al.; 'Oxyntomodulin Inhibits Food Intake in the Rat'; Endocrinology; V. 142; pp. 4244-4250; 2001.

Dakin et al.; 'Peripheral Oxyntomodulin Reduces Food Intake and Body Weight gain in Rats'; Endocrinology; V. 145; No. 6; pp. 2687-2695; Jun. 2004.

Davison; 'Activation of Vagal-Gastric Mechanoreceptors by Cholecystokinin'; Proc. West. Pharmocol. Soc; V. 29; pp. 363-366; 1986.

De Waele et al.; "Endoscopic Volume Adjustment of Intragastric Balloons for Intolerance"; Obesity Surgery; V. 11; pp. 223-224; 2001.

De Waele et al.; "Intragastric Balloons for Preoperative Weight Reduction"; Obesity Surgery; V. 58; pp. 58-60; 2001.

Desai et al.; 'Molecular Weight of Heparin Using 13C Nuclear Magnetic Resonance Spectroscopy' Journal of Pharmaceutical Science, V. 84,12; 1995, Abstract only.

Doldi et al.; 'Intragastric Balloon: Another Option for Treatment of Obesity and Morbid Obesity'; Hepato-Gastroenterology; V. 51, N. 55; pp. 294-307; Jan.-Feb. 2004.

Doldi et al.; 'Treatment of Morbid Obesity with Intragastric Balloon in Association with Diet'; Obesity Surgery; V. 10, pp. 583-587; 2000.

Ekblad et al.; 'Distribution of Pancreatic Peptide and Peptide-YY'; Peptides; V. 23; pp. 251-261;2002.

El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.

Galloro et al; "Preliminary Endoscopic Technical Report of an New Silicone Intragastric Balloon in the Treatment of Morbid Obesity"; Obesity Surgery; V. 9, pp. 68-71; 1999.

GinShiCel MH Hydroxy Propyl Methyl Cellulose, Web Page http://www.ginshicel.cn/MHPC.html, Nov. 12, 2008.

Girard; 'The Incretins: From the concept to their use in the treatment of type 2 diabetes. Part A: IncretinsIncretinsIncretinsIncretinsIncretins: Concept and physiological functions'; Diabetes and Metabolism; V. 34; pp. 550-559; 2008.

Greenough et al.; 'Untangling the Effects of Hunger, Anxiety and Nausea on Energy Intake During Intravenous Cholecystokinin Octapeptide (CCK-8) Infusion' Physiology and Behavior; V. 65 (2); pp. 303-310; 1998.

Grise et al.; "Peptide YY Inhibits Growth of Human Breast Cancer in Vitro and in Vivo"; Journal of Surgical Research; V. 82; pp. 151-155; 1999.

Grundy; "Signaling the State of the Digestive Tract"; Autonomic Neuroscience: Basic and Clinical; V. 125; pp. 76-80; 2006.

Grundy; "Vagal Control of Gastrointestinal Function"; Bailliere's Clinical Gastroenterology; V. 2; No. 1; pp. 23-43; 1988.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Hameed et al., 'Gut Hormones and Appetite Control', Oral Diseases, 2009, 15:18-26.

(56) References Cited

OTHER PUBLICATIONS

Hassan et al.; 'Effects of Adjuvants to Local Anesthetics on Their Duration III Experimental Studies of Hyaluronic Acid' Abstract Pub Med [Acta Anesthesiol Scand.; 29 (4): 384-8], 1 page; May 1985.
Hodson et al.; 'Management of Obesity with the New Intragastric Balloon'; Obesity Surgery; V. 11, pp. 327-329,2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.
Houpt; 'Gastrointestinal Factors in Hunger and Satiety'; Neurosci. and Behav. Rev.; V. 6; pp. 145-164; 1982.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; 'Exogenous Ghrelin Enhances Endocrine and Exocrine Regeneration in Pancreatectomized Rats'; J. Gastrointest Surg.; V. 13; pp. 775-783, 2009.
Kesty et al., 'Hormone-based Therapies in the Regulation of Fuel Metabolism and Body Weight', Expert Opin. Biol. Ther., 2008, 8(11): 1733-1747.
Kissileff et al.; 'Peptides that Regulate Food Intake: Cholecystokinin and Stomach Distension Combine to Reduce Food Intake in Humans'; Am. J. Physiol. Regul. Integr. Comp. Physiol.; V. 285; pp. 992-998; 2003.
Kojima et al., 'A Role for Pancreatic Polypeptide in Feeding and Body Weight Regulation', Peptides, 2007, 28:459-463.
Kulicke et al. "Visco-Elastic Propeerties of Sodium Hyaluronate Solutions," American Institute of Physics; pp. 585-587; 2008.
Lap-Band AP System Adjustable Gastric Banding System With OmniformTM Design: Directions for Use (DFU); Allergan, 16 pages; 2009.
Le Roux et al.; 'Gut Hormone Profiles Following Bariatric Surgery Favor an Anorectic State, Facilitate Weight Loss, and Improve Metabolic Parameters'; Ann. Surg; V. 243; No. 1; pp. 108-114; Jan. 2006.
Liu et al.; 'Adjuvant Hormonal Treatment With Peptide YY or Its Analog Decreases Human Pancreatic Carcinoma Growth'; The American Journal of Surgery; V. 171; pp. 192-196; Jan. 1996.
Mathus-Vliegen et al. 'Intragastric Balloons for Morbid Obesity: Results, Patient Tolerance and Balloon Life Span'; Br. J. Surg.; V. 77, No. 7, pp. 76-79; Jan. 1990.
Mathus-Vliegen et al. "Treating Morbid and Supermorbid Obesity" International Journal of Gastroenterology; V. 5, No. 1, pp. 9-12; 2000.
Medeiros et al.; 'Processing and metabolism of Peptide-YY: Pivotal roles of Dipeptidase-IV, Aminopeptidase-P, and Endopeptidase-24. 11'; Endocrinology; V. 134, No. 5; pp. 2088-2094;1994.
Naslund et al.; 'Prandial Subcutaneous Injection of Glucagon-Like Peptide'; Br. J. Nutr.; V. 91; pp. 439-446; 2004.
Potier et al.; "Protein, amino acids, and the control of food intake"; Current Opinion in Clinical Nutrition and Metabolic Care; V. 12; pp. 54-58; 2009.
Qjan et al.; 'Pulmonary delivery of a GLP-1 receptor agonist, BMS-686117'; International Journal of Pharmaceutics; V. 366; pp. 218-220; 2008.
Rang et al.; 'Pharmacology'; V. 5; pp. 203, 397,402, 524; 2004.
Raybould et al.; "Integration of Postprandial Gastrointestinal Tract: Role of CCK and Sensory Pathways"; Annals of New York Academy of Science; pp. 143-156; 1994.
Renshaw et al. 'Peptide YY: A Potential Therapy for Obesity'; Current Drug Targets; V. 6; pp. 171-179; 2005.
Sannino et al., 'Crosslinking of Cellulose Derivatives and Hyaluronic Acid with Water-Soluble Carbodiimide,' Polymer 46(2005)pp. 11206-11212.
Shechter et al.; "Reversible PEGylation of peptide YY3-36 prolongs its inhibition of food intake in mice"; FEBS Letters; V. 579; pp. 2439-2444; 2005.

Silver et al.; 'Physical Properties of Hyaluronic Acid and Hydroxypropylmethylcellulose in Solution: Evaluation of Coating Ability' Journal of Applied Biomaterials, V. 5; pp. 89-98, 1994.
Small et al.; 'Gut hormones and the control of appetite'; Trends in Endocrinology and Metabolism; V. 15; No. 6; pp. 259-263; Aug. 2004.
Stanley et al.; 'Gastrointestinal Satiety Signals III. Glucagon-like Peptide 1, oxyntomodulin, peptide YY, and pancreatic polypeptide'; Am. J. Physiol Gastrointest Liver Physiol; V. 286; pp. 693-697; 2004.
Tezel, 'The Science of Hyaluronic Acid Dermal Fillers,' Journal of Cosmetic and Laser Therapy (2008) 10: pp. 35-42.
Tolhurst et al.; 'Nutritional regulation of glucagon-like peptidel secretion'; J. Physiol.; V. 587, No. I;pp. 27-32; 2009.
Totte et al.; "Weight Reduction by Means of Intragastric Device: Experience with the Bioenterics Intragastric Balloon"; Obesity Surgery; V. 11, pp. 519-523; 2001.
Tough et al.; 'Y4 Receptors Mediate the Inhibitory Responses of Pancreatic Polypeptide in Human and Mouse Colon Mucosa'; The Journal of Pharmacology and Experimental Therapeutics; V. 319, No. 1; pp. 20-30; 2006.
Tseng et al; "Peptide YY and cancer: Current findings and potential clinical applications"; Peptides; V. 23; pp. 389-395; 2002.
Valassi et al.; "Neuroendocrine control of food intake"; Nut. Metab. & Cariovasc. Disease; V. 18; pp. 158-168; 2008.
Van Der Lely et al.; "Biological, Physiological, Pathophysiological Aspects of Ghrelin"; Endocrine Reviews; V. 25, No. 3; pp. 426-457; 2004.
Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.
Wahlen et al.; 'The BioEnterics Intragastric Balloon (BIB): How to Use It'; Obesity Surgery; V. 11; pp. 524-527; 2001.
Wang et al.; "Plasma Ghrelin Modulation in Gastric Band Operation and Sleeve Gastrectomy"; Obes. Surg.; pp. 357-362; 2008.
Weiner et al.; 'Preparation of Extremely Obese Patients for Laparoscopic Gastric Banding by Gastric Balloon Therapy'; Obesity Surgery; V. 9, pp. 261-264, 1999.
Wynne et al.; 'Subcutaneous Oxyntomodulin Reduces Body Weight in Overweight and Obese Subjects: A Double-Blind Randomized, Controlled Trial': Diabetes; V. 54; pp. 2390-2395; 2005.
Yuzuriha et al.; "Gastrointestinal Hormones (anorexigenic peptide YY and orexigenic ghrelin) influence neural tube development"; FASEB J.; V. 21; pp. 2108-2112; 2007.
Brown et al; 'Symmetrical Pouch Dilation After Laparoscopic Adjustable Gastric Banding: Incidence and Management'; Obesity Surgery; V. 18, pp. 1104-1108; 2008.
Ceelen et al.; 'Surgical Treatment of Severe Obesity With a Low-Pressure Adjustable Gastric Band: Experimental Data and Clinical Results in 625 Patients'; Annals of Surgery; V. 237, No. I;pp. 10-16; 2003.
Dixon et al.; 'Pregnancy After Lap-Band Surgery: Management of the Band to Achieve Healthy Weight Outcomes'; Obesity Surgery; V. 11, pp. 59-65; 2001.
Neary et al.; 'Peptide YY(3-36) and Glucagon-Like Peptide-1.sub. (7-36) Inhibit Food Intake Additively'; Endocrinology; V.146; pp. 5120-5127; 2005.
Padidela et al.; 'Elevated basal and post-feed glucagon-like petide 1 (GLP-1) concentrations in the neonatel period'; European Journal of Endocrinology; v. 160; pp. 53-58; 2009.
Shi et al; 'Sexually Dimorphic Responses to Fat Loss After Caloric Restriction or Surgical Lipectomy'; Am. J. Physiol. Endocrinol. Metab.; V. 293; E316-E326; 2007.
Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.

\* cited by examiner

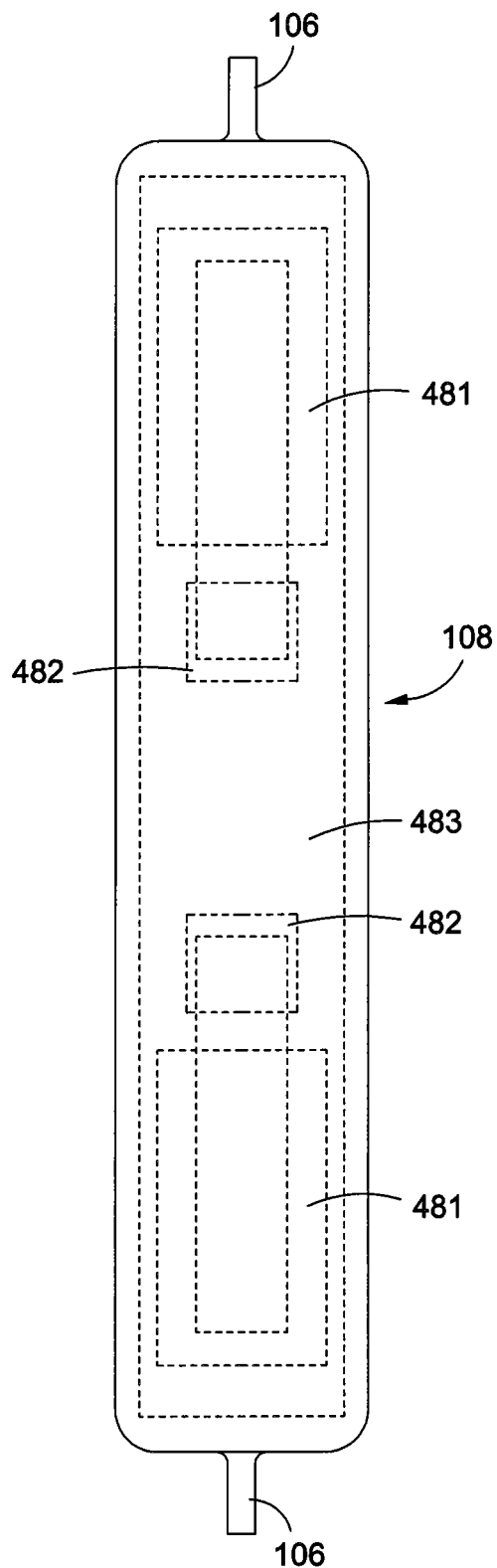
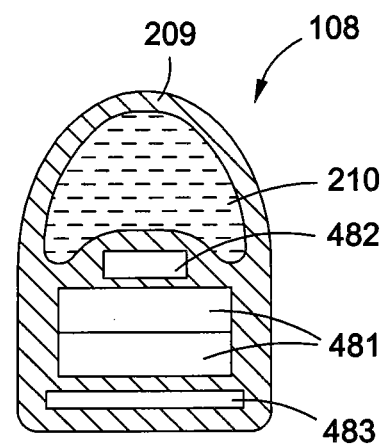
FIG. 4A
FIG. 4B

REMOTELY ADJUSTABLE GASTRIC BANDING SYSTEM

CROSS REFERENCE TO RELATED APPLICATIONS

This application is a continuation of U.S. patent application Ser. No. 12/877,046, filed Sep. 7, 2010, the contents of which is incorporated herein by reference.

FIELD

The present invention generally relates to medical systems and apparatus and uses thereof for treating obesity and/or obesity-related diseases, and more specifically, relates to gastric banding systems that are remotely adjustable.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, the food is held in the upper portion of the stomach provides a feeling of satiety or fullness that discourages overeating. Unlike gastric bypass procedures, gastric band apparatus are reversible and require no permanent modification to the gastrointestinal tract.

Over time, a stoma created by a gastric band may need adjustment in order to maintain an appropriate size, which is neither too restrictive nor too passive. Accordingly, prior art gastric band systems provide a subcutaneous fluid access port connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction. Naturally, it would be desirable to allow for non-invasive adjustment of gastric band constriction, for example, without the use of a hypodermic needle.

A remotely adjustable gastric band is a medical device which allows a healthcare worker to adjust a gastric band without utilizing hypodermic needles to connect to an implanted access port. A handheld controller may be used to send radio frequency waves for powering and communicating with the implanted device. The implanted device can fill or drain the gastric band as requested by the healthcare worker via the handheld controller.

Birk, et al., U.S. Patent Pub. No. 2007/0265645, and Birk, U.S. Patent Pub. No. 2007/0156013, which are commonly-assigned and co-pending with the present application, are incorporated herein in their entirety by this specific reference. Both of these applications disclose certain approaches to implantable pumping systems that may be relevant.

Some versions of remotely adjustable gastric band systems may include a receiving coil for power induction to drive the pump. However, the location and/or orientation of the receiving coil may not provide desired power to the pump and/or other system components. Furthermore, the presence of metallic objects near the receiving coil may adversely affect the power provided to the system.

Additionally, some attempts have been made to utilize a remotely driven pump to inflate an inflatable portion of a gastric band. For example, Hassler, Jr., et al., U.S. Patent Pub. Nos. 2006/0252982 and 2005/0288739; Hassler, Jr., U.S. Pat. No. 7,390,294, and U.S. Patent Pub. Nos. 2005/0267406 and 2005/0267500; and Jordan, et al., U.S. Patent Pub. No. 2008/0108862 generally disclose remote adjustment of a gastric band. However, the location and/or position of the induction coils in these systems may not provide the desired energy for the system.

Thus, there continues to be a need for more effective remotely adjustable gastric banding systems, particularly for systems that have more available power for driving the implantable pump and/or other system components. Further, there is a need for remotely adjustable gastric banding systems that have a more effective electric coil for receiving transmitted energy.

SUMMARY

Generally described herein are remotely adjustable and powered gastric banding systems. The apparatus and systems described herein aid in facilitating obesity control and/or treating obesity-related diseases while being non-invasive once implanted.

In an embodiment, a fluid reservoir for use in the remotely adjustable gastric banding system comprises a housing and a flexible reservoir pouch positioned within the housing. The flexible reservoir pouch is coupled to an inflatable portion of a gastric band via flexible tubing. A pump coupled to the flexible reservoir pouch facilitates filling and draining of the inflatable portion of the gastric band.

In another embodiment, a receiving coil may be coupled to the housing, and the receiving coil forms a loop around the housing. For example, the receiving coil may be disposed in a coil channel along the periphery of the housing. The receiving coil receives radio frequency signals from a remote transmitter to drive the pump coupled to the flexible reservoir pouch. Certain embodiments may include two receiving coils disposed along the periphery of the housing to facilitate enhanced energy reception by the coils.

According to another embodiment, the pump may be disposed in the housing and coupled to the flexible reservoir pouch via a valve. Some embodiments include a plurality of pumps, each coupled to the flexible reservoir pouch. The pumps move a fluid in the flexible reservoir pouch between the flexible reservoir pouch and the inflatable portion of the gastric band.

A circuit board may also be disposed in the housing for driving the pump to move the fluid between the flexible reservoir pouch and the inflatable portion of the gastric band. At least a portion of the circuit board may be a flexible circuit board to allow the housing to flex.

BRIEF DESCRIPTION OF THE DRAWINGS

FIG. 4A illustrates a sectional view of a fluid reservoir with pumps and a circuit board according to an embodiment of the present invention.

FIG. 4B illustrates another sectional view of a fluid reservoir with pumps and a circuit board according to an embodiment of the present invention.

DETAILED DESCRIPTION

The present invention generally provides remotely adjustable gastric banding systems, for example, for treatment of obesity and obesity related conditions, as well as systems for controlling inflation and deflation of gastric banding systems.

A remotely adjustable gastric band is a medical device which allows a healthcare worker to adjust a gastric band without utilizing hypodermic needles to connect to an implanted access port. An external, handheld controller can be used to send radio frequency signals for powering and communicating with the implanted device. The implanted device can fill or drain the gastric band as requested by the healthcare worker via the handheld controller. The handheld controller may be a remote device configured to produce a telemetric signal that controls the various components of the gastric banding system.

The filling and draining of the band is accomplished by a set of fluidic elements including pumps, valves, and sensors which monitor and/or move fluid between the gastric band and a reservoir. In accordance with various embodiments, different numbers, types, and orientations of the fluidic elements may be utilized to obtain the desired results. Any and/or all of these various components may be configured to be controlled by a remote transmitter, such as a handheld controller.

Figure 1A:
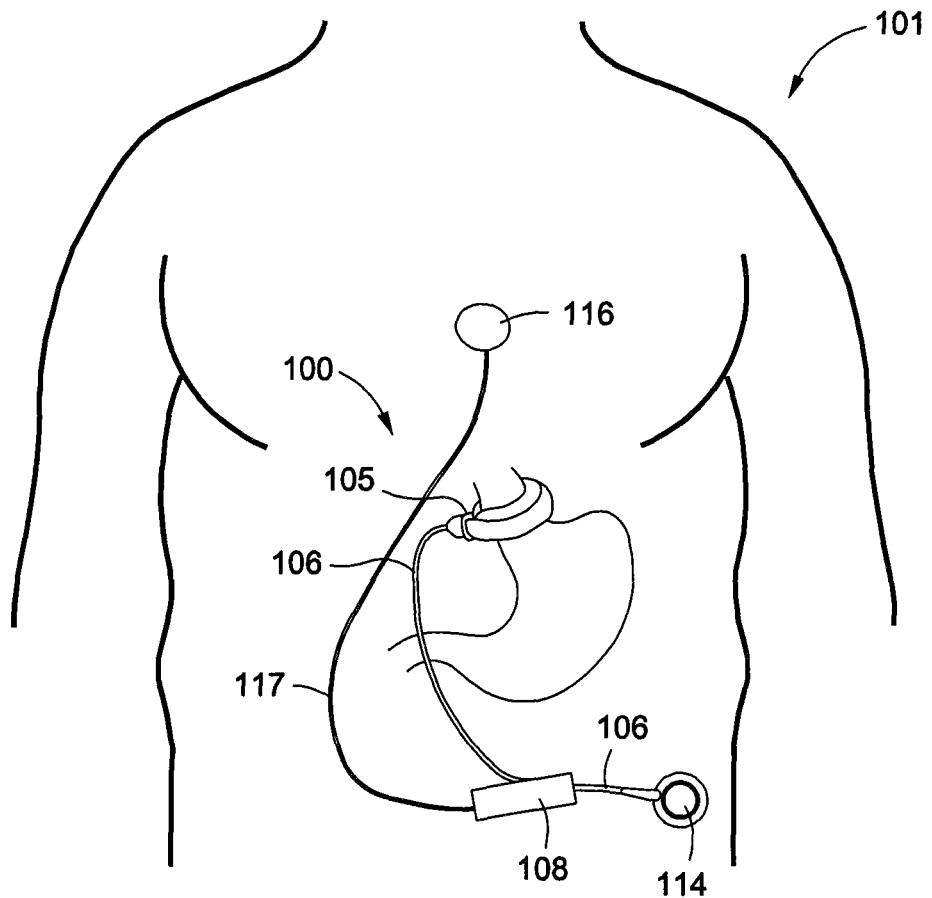
FIGS. 1A and 1B illustrate a location of a gastric banding system within a patient's body according to an embodiment of the present invention.
Figure 1B:
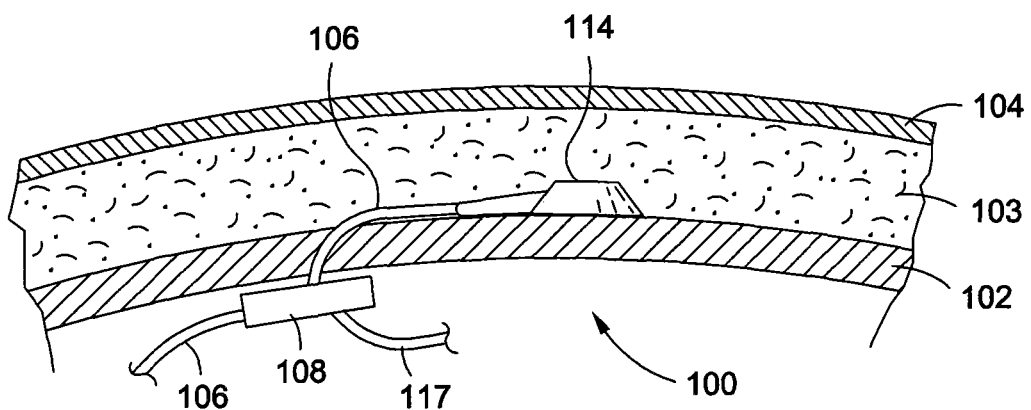

Turning now to FIGS. 1A-1B, in accordance with an embodiment, a gastric banding system 100 includes a gastric band 105, a reservoir unit 108, an access port 114, and a receiving coil 116. The flexible tubing 106 connects the gastric band 105 and the access port 114 to the reservoir unit 108. Each of the components of the system 100 is implantable in a patient using conventional surgical techniques. The reservoir unit 108 and the coil unit 116 may be used instead of or in addition to the conventional access port 114. In various embodiments, as will be discussed further below, the coil unit 116 may be incorporated into other components of the gastric banding system 100.

The reservoir unit 108 may move precisely metered volumes of fluid (e.g., saline, a drug, and/or combinations thereof) from the reservoir unit 108 through the flexible tubing 106 into the gastric band 105. The reservoir unit 108 may comprise a compressible reservoir, such as an elastic polymer, a balloon, a rubber container, a silicone container, a collapsible container, a non-elastomeric container, a bellows, and combinations thereof that are configured to contain the fluid. The gastric banding system 100 may include various pumps, motors, and the like that are configured to facilitate filling or draining the gastric band 105 by moving fluid between the reservoir unit 108 and the gastric band 105. The various pumps, motors, and the like may be separate components of the system 100, or they may be incorporated into existing components. For example, the reservoir unit 108 may comprise pumps, motors, and the like.

Moving the fluid into the gastric band 105 causes inflation of at least one bladder, or inflatable member of the gastric band 105, and constricts around the cardia, or upper portion of the stomach, forming a stoma that restricts the passage of food into a lower portion of the stomach. This stoma may provide a patient with a sensation of satiety or fullness that discourages overeating. In contrast, moving the fluid out of at least one inflatable member of the gastric band 105 contracts the pressure around the cardia and allows a stoma to be at least partially released and regains the patient's hunger sensation.

The receiving coil 116 receives radio frequency signals from an external/remote handheld controller or transmitter to control operation of the system 100. For example, the receiving coil 116 receives radio frequency energy to provide power to various system components (e.g., a pump, a motor, a circuit board, and the like). As noted above, and as will be discussed further below, the receiving coil 116 may be located in or near other components of the gastric banding system 100, such as in or near the reservoir unit 108 or the access port 114.

Although "transmitter" may be used herein, it should be understood that the remote transmitter may also be a wireless receiver and/or transceiver operable to take readings from the system 100 to determine the amount of fluid entering and/or exiting the gastric band 105, and/or to send or receive other types of information associated with the gastric banding system 100.

In accordance with various embodiments, the gastric banding system 100 allows for a remotely controlled adjustment without needles, non-invasively, by using the remote transmitter. A conventional access port 114 may be included as part of system 100 in order to provide alternate filling and draining capabilities, for example, to provide a fail-safe alternative in case the non-invasive functionality (e.g., motor, electronics, driving mechanism) becomes inoperative and/or ineffective. The access port 114 may be used to extract fluid from the system in case of an emergency or as a safety measure. However, non-invasively filling and draining the gastric band 105 using the reservoir unit 108 represents advantages over gastric banding systems that only use standard access ports. The access port 114 may further be used to prime the system with a desired amount of fluid upon implantation.

When compared to conventional gastric banding systems having standard access ports which exclusively require syringe access, the presently described systems and apparatus offer several benefits. First, for conventional access ports located under a thick layer of fatty tissue, which is generally the case as the devices are typically used to treat obesity, the access port can be difficult to locate. The present systems reduce or eliminate the need for port location as the use of the remote transmitter removes the necessity of adjustment using a syringe.

In various embodiments, the access port 114 may be incorporated into other system components in order to provide for backup and/or emergency filling and draining of the gastric band (e.g., when the remote filling and draining functionalities are ineffective or unresponsive). For example, an implantable pump may incorporate the access port 114 and may be implanted at a location similar to where the access port 114 may be implanted. Such an implantable pump may be referred to as a gastric restrictive implantable pump. The implantable pump may further include fluidics (e.g., pumps and valves) and associated electronics. In some embodiments, the receiving coil 116 for power induction may be included within the implantable pump housing. However, the size of the implantable pump housing, the depth of the implantable pump (e.g., up to four or more inches), and the presence of metal within the housing may affect the ability to achieve specific power requirements.

According to various embodiments, components of the gastric banding system 100 may be placed in their respective positions within a patient 101 using common surgical techniques. The surgical techniques may be similar to those used in the placement of conventional gastric banding systems. For example, the gastric band 105 may be placed around the stomach using laparoscopic techniques, as known to those of skill in the art.

Like a conventional access port, various components of the gastric banding system 100 may be sutured onto the rectus muscle sheath 102 or any other conveniently accessible muscle. For example, the access port 114 and/or the reservoir unit 108 may be sutured to the rectus muscle sheath 102. The rectus muscle sheath 102 provides a secure surface on which to attach the access port 114 under a layer of fat 103 that separates the patient's skin 104 from the muscle 102.

The receiving coil unit 116 may be located near the sternum of the patient 101, and a wire 117 may electronically couple the receiving coil unit 116 to the reservoir unit 108. In an embodiment, the reservoir unit 108 is located in the peritoneal cavity of the patient 101. In other embodiments, the components of the system 100 may be positioned in other locations in the patient 101 to facilitate filling or draining of the gastric band 105. For example, in an embodiment, the access port 114 may be incorporated into the reservoir unit 108, such that the reservoir unit 108 may be implanted on the rectus muscle sheath.

Figure 2A:
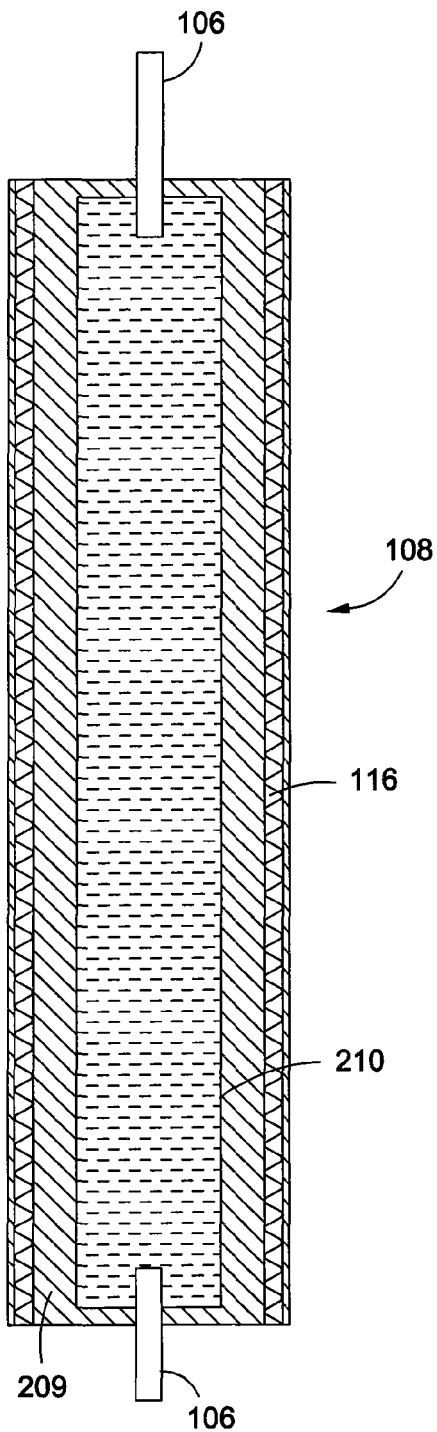
FIG. 2A illustrates a sectional view of a fluid reservoir with a receiving coil according to an embodiment of the present invention.
Figure 2B:
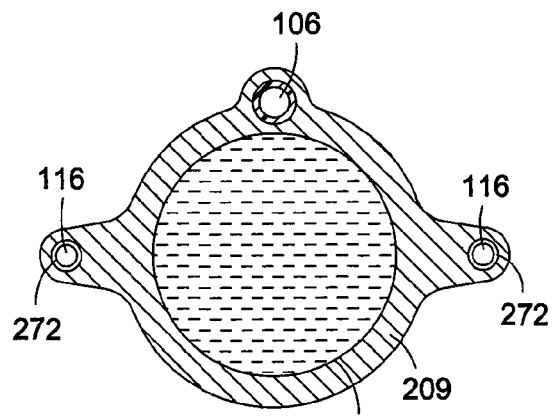
FIG. 2B illustrates another sectional view of a fluid reservoir with a receiving coil according to an embodiment of the present invention.
Figure 2C:
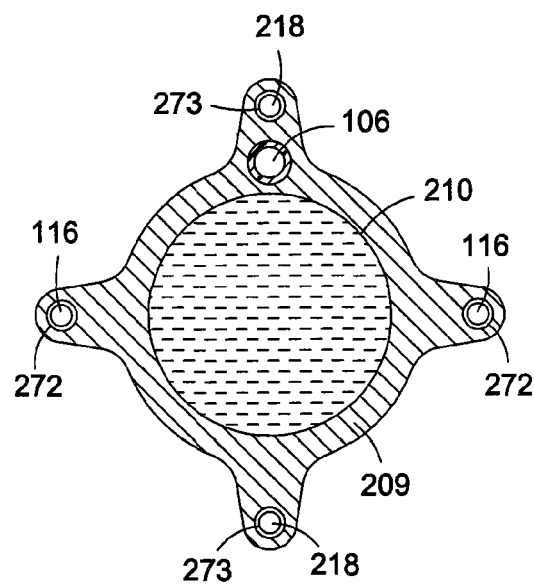
FIG. 2C illustrates a sectional view of a fluid reservoir with two receiving coils according to an embodiment of the present invention.

Turning to FIGS. 2A-2C, in various embodiments, the reservoir unit 108 comprises a housing 209 that is generally and/or substantially cylindrical in shape. Other shapes may be used without departing from the scope of the present invention. The housing 209 may be flexible, semi-flexible, semi-rigid, and/or rigid. A reservoir, such as a flexible reservoir pouch 210 is disposed in the housing 209. The flexible reservoir pouch 210 may be a compressible pouch, an elastic polymer, a balloon, a rubber container, a silicon container, and/or combinations thereof. Further, the flexible reservoir pouch 210 may be formed in the shape of a donut, a circle, an ellipse, a rectangle, and combinations thereof.

In an embodiment, the coil 116 may be implemented at the level of the reservoir unit 108, for example, by winding the coil 116 around the reservoir unit 108. The housing 209 of the reservoir unit 108 may comprise a coil channel 272 that receives the coil 116 and orients the coil 116 in a loop around the reservoir unit 108. The coil channel 272 may extend along the sides of the housing 209, extend parallel to a central axis of the housing 209, and/or extend around/along the periphery of the housing 209.

In various embodiments, the coil 116 is wound around the periphery of the reservoir unit 108 so as to be near the surface of the housing 209. In such a configuration, less of the material of the housing 209 would interfere with the induction between the coil 116 and the external transmitter. Further, locating the coil 116 near the periphery of the housing 209 would place the coil 116 nearer the transmitter to increase the power made available to the system 100.

Where the coil 116 forms a single loop around the reservoir unit 108, more power will be induced into the system 100 when the coil 116 is parallel to the skin surface 104 of the patient 101, compared to the coil 116 being perpendicular to the skin surface 104. In an embodiment, the reservoir unit 108 may be sutured in place to properly orient the coil 116 with respect to the skin surface 104, for example, so that the loop formed by the coil 116 is substantially parallel to the skin surface 104.

Other embodiments account for the situation where the coil 116 may be perpendicular to the skin surface 104. For example, with particular reference to FIG. 2C, and in accordance with an embodiment, the coil 116 may form one loop around the housing 209 through the coil channels 272, and a second coil 218 may form a second loop around the housing 209 and through coil channels 273. The coils 116 and 218 may be substantially perpendicular to each other, so that if one coil is oriented perpendicularly with respect to the skin surface 104, the other coil would be substantially parallel to the skin surface 104, allowing the parallel coil to pick up the RF energy from the transmitter.

In other embodiments, both of the coils 116 and 218 may pick up RF energy from the transmitter, for example, where neither of the coils 116 and 218 are perpendicular to the skin surface 104. As such, the energy picked up from both of the coils 116 and 218 would need to be added.

Figure 3:
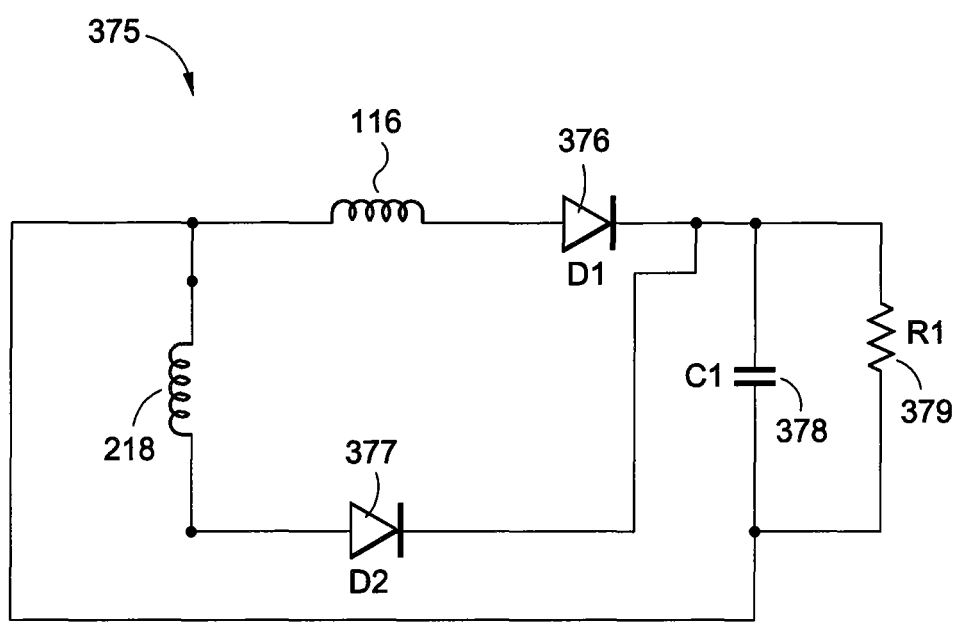
FIG. 3 illustrates a center tap circuit for adding energy received through two receiving coils according to an embodiment of the present invention.

With reference to FIG. 3, and in accordance with an embodiment, the energy from the coils 116 and 218 may be added through a circuit, such as a center tap 375. A resistor (R1) 379 and a capacitor (C1) 378 may represent the load of the system 100. A rectifying diode 376 is coupled to the coil 116, and a rectifying diode 377 is coupled to the second coil 218. The rectifying diodes 376 and 377 restrict the flow of current from the coils 116 and 218 to one direction into the capacitor 378 and the resistor 379. In various embodiments, depending on the orientation of the coils 116 and 218, the center tap 375 may result in half-wave rectification. It should be understood that other circuits and/or components may be utilized to facilitate transferring inducted energy from the coils 116 and 218 to the components of the system 100 that utilize the energy, and that such other circuits and/or components are within the scope of the present invention.

In accordance with various embodiments, circuitry, such as the center tap circuit 375 may be located in or near the reservoir unit 108. In other embodiments, the circuitry may be located in or near other components of the system 100, such as in or near the access port 114.

Where the coils 116 and 218 are looped around the reservoir unit 108, in an embodiment, tuning capacitors may also be located in or near the reservoir unit 108. The tuning capacitors may facilitate adjusting the resonant frequency of the system, and locating the tuning capacitors closer to the coils 116 and 218 advantageously results in proper adjustment of the resonant frequency. For example, locating the tuning capacitors further away from the coils 116 and 218 may result in greater parasitic capacitance.

Further, in accordance with various embodiments, it may be desirable to reduce the distance between the skin surface 104 and the coils 116 and 218 which are looped around the reservoir unit 108. For example, the RF coupling between the transmitter and the coils 116 and 218 is inversely proportional to the distance between the coils 116 and 218 and the transmitter by a power of approximately 3. In other words, the closer the coils 116 and 218 are to the skin surface 104, the more RF energy may be received by the coils 116 and 218, resulting in more power for the system 100. Therefore, in various embodiments, the coils 116 and 218 are advantageously located near the skin surface 104.

Configurations of the system 100 according to embodiments of the present invention remedy deficiencies in prior art systems where the prior induction coils may be located in a manner that reception by the coils is poor. On the other hand, embodiments of the present invention increase energy reception by the coils 116 and 218 due to the advantageous location and configuration of the coils 116 and 218.

As noted above, in various embodiments, a pump may be located in or near the access port 114. In other embodiments, and with reference to FIGS. 4A-4B, a pump or pumps 481 may be located within the reservoir unit 108. Further, other components of the system 100 may be located within or near the reservoir unit 108 to facilitate simpler implantation of the system 100. Where other components are contained within the reservoir unit 108, the reservoir housing 209 may be semi-flexible, semi-rigid, and/or rigid. In various embodiments, currently existing access ports may be coupled to the reservoir unit 108 resulting in simpler and less expensive incorporation of the reservoir unit 108 into existing gastric banding systems.

In an embodiment, where the pumps 481 are located within the reservoir unit 108, the coil 116 may also be located within or around the reservoir unit 108, as discussed above. However, as illustrated in FIG. 1A, the coil 116 may be located near the sternum to facilitate increased power inducted through the coil 116. Although the pumps 481 may be described herein as being located within the reservoir unit 108, it should also be understood that various embodiments of the invention include systems 100 where the reservoir unit 108, the pumps 481, and/or other components may be located in or near the access port 114 to facilitate simpler implantation of the system 100.

With continued reference to FIGS. 4A-4B, various embodiments of the present invention include a pump or pumps 481 disposed in the housing 209 of the reservoir unit 108. The valves 482 couple the pumps 481 to the flexible reservoir pouch 210. The pumps 481 are also coupled to the tubing 106 to facilitate moving fluid between the flexible reservoir pouch 210 and the inflatable portion of the gastric band 105. The pumps 481 are coupled to a circuit board 483, such as a flexible circuit board, which drives the pumps 481. In an embodiment, the flexible reservoir pouch 210 comprises a flaccid reservoir on top of fluidic and electronic elements such as the pumps 481, the valves 482, and the circuit board 483. The flexible reservoir pouch 210 adds flexibility to the reservoir unit 108, for example, in the cross-sectional plane.

The circuit board 483 may include various circuits for driving the gastric banding system 100. For example, the circuit board 483 may include the center tap circuit 375 for adding the signals received through the coils 116 and 218.

The pumps 481 operate on the fluid in the flexible reservoir pouch 210 to facilitate moving the fluid between the flexible reservoir pouch 210 and the inflatable portion of the gastric band 105. In an embodiment, the pumps 481 comprise piezoelectric pumps. Further in an embodiment, each pump 481 may comprise two or more piezoelectric actuators to increase pumping capability without adding additional pumps. For example, in an embodiment, six piezoelectric actuators may be utilized to provide the desired pumping capability, but these six actuators may be included in only three pumps 481 which allows for a reduced amount of space needed in the housing 209 for the pumps 481. In other embodiments, more or fewer pumps 481 or piezoelectric actuators may be utilized depending on the designed pumping capacity. Additionally, other types of pumps may be utilized without departing from the scope of the present invention.

In various embodiments, the circuit board 483 may comprise a flexible circuit board. The entire circuit board 483 may be a flexible circuit board, or only portions of the circuit board 483 may comprise a flexible circuit board. In an embodiment, the center of the circuit board 483 is a flexible circuit board to allow the reservoir unit 108 to flex in the middle of the unit 108.

As noted above, the coil 116 may be looped around the reservoir unit 108, or the coil 116 may be located near the sternum of the patient 101, or in another advantageously determined location. Locating the coil 116 around the periphery of the reservoir unit 108 may allow the coil 116 to have a larger area for increased power transfer. However, locating the coil 116 near the sternum may allow the coil 116 to be nearer the skin surface 104 to also allow for increased power transfer. Thus, depending on the patient 101 and/or other variables, some embodiments comprise the coil 116 near the sternum, and other embodiments comprise the coil 116 near the reservoir unit 108. Locating the coil 116 near the reservoir unit 108 as opposed to near the access port 114 reduces the amount of metallic elements near the coil 116, which in turn increases the amount of RF energy available to be absorbed by the coil 116. Locating the coil 116 near the reservoir unit 108 also reduces the length of the wiring utilized to couple the coil 116 to the pumps 481, thereby advantageously reducing the possibility that these wires will fail.

Various embodiments of the present invention provide for modular design of gastric banding system 100. For example, the reservoir unit 108 may contain components that allow a remotely adjustable gastric banding system to be utilized in connection with access ports that are currently used in existing gastric banding systems. Thus, a physician may have the option of implanting an existing system or a system 100 according to embodiments of the present invention depending on the circumstances of a particular implantation procedure.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventor for carrying out the invention. Of course, variations on these described embodiments will become apparent to those of ordinary skill in the art upon reading the foregoing description. The inventor expects skilled artisans to employ such variations as appropriate, and the inventor intends for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using "consisting of" and/or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A fluid reservoir for connecting to a remotely adjustable gastric banding system that is implantable in a patient for the treatment of obesity, the fluid reservoir comprising:
    a housing defining separately enclosed first and second coil channels;
    a flexible reservoir pouch positioned within the housing and coupled to an inflatable portion of a gastric band via tubing, the flexible reservoir pouch for storing a fluid for filling and draining the inflatable portion of the gastric band;
    a first receiving coil coupled to the housing and extending within the first coil channel, wherein the first receiving coil forms a first loop around the housing, and wherein the first receiving coil receives radio frequency signals from a remote transmitter to drive a pump in the remotely adjustable gastric banding system; and
    a second receiving coil coupled to the housing and extending within the second coil channel, wherein the second receiving coil forms a second loop around the housing.

2. The fluid reservoir of claim 1, wherein the housing is substantially cylindrical.

3. The fluid reservoir of claim 1, wherein the housing is at least one of flexible, semi-flexible, rigid, or semi-rigid.

4. The fluid reservoir of claim 1, wherein the housing has sides and defines a central axis, and the first coil channel extends along the sides of the housing, substantially parallel to the central axis of the housing.

5. The fluid reservoir of claim 1, wherein the first loop formed by the first receiving coil defines a plane, and when the fluid reservoir is in an implanted condition, the plane is oriented substantially parallel to an overlying skin surface of the patient.

6. The fluid reservoir of claim 5, wherein the housing is adapted to be sutured to a muscle of a patient to facilitate maintaining the loop of the first receiving coil substantially parallel to the overlying skin surface.

7. The fluid reservoir of claim 1, wherein the second receiving coil forms a second loop around the housing.

8. The fluid reservoir of claim 7, wherein the first loop formed by the first receiving coil is substantially perpendicular to the second loop formed by the second receiving coil.

9. The fluid reservoir of claim 8, further comprising a center tap circuit for adding the radio frequency signals received through the first receiving coil and the second receiving coil when both the first receiving coil and the second receiving coil receive the radio frequency signals.

10. The fluid reservoir of claim 9, wherein the center tap circuit comprises a first rectifying diode coupled between the first receiving coil and a load so that current from the first receiving coil is restricted to one direction.

11. The fluid reservoir of claim 10, wherein the center tap circuit comprises a second rectifying diode coupled between the second receiving coil and the load.

12. The fluid reservoir of claim 1, further comprising a pump disposed within the housing to move fluid between the flexible reservoir pouch and the inflatable portion of the gastric band, wherein the pump receives energy from the radio frequency signals received through the first receiving coil.

13. The fluid reservoir of claim 12, further comprising a circuit board for driving the pump.

14. The fluid reservoir of claim 13, wherein at least a portion of the circuit board comprises a flexible circuit board.

15. The fluid reservoir of claim 12, wherein the pump is a piezoelectric pump comprising a piezo actuator.

16. The fluid reservoir of claim 12, wherein the pump is a piezoelectric pump comprising a plurality of piezo actuators.

17. The fluid reservoir of claim 1, wherein the housing is flexible.

18. The fluid reservoir of claim 1, wherein the reservoir pouch is elastic.

* * * * *